United States Patent [19]

Erlich

[11] Patent Number: 5,595,185

[45] Date of Patent: Jan. 21, 1997

[54] SINGLE PUNCTURE MULTI-BIOPSY GUN

[75] Inventor: Nahum Erlich, Ramat Gan, Israel

[73] Assignee: N.M.B. Medical Applications Ltd., Caeseria, Israel

[21] Appl. No.: 289,115

[22] Filed: Aug. 11, 1994

[51] Int. Cl.$^6$ .................................................. A61B 10/00
[52] U.S. Cl. ................................................................. 128/754
[58] Field of Search ........................... 128/749, 751–754; 606/167, 170

[56] References Cited

U.S. PATENT DOCUMENTS

| | | | |
|---|---|---|---|
| 4,600,014 | 7/1986 | Beraha | 128/754 |
| 4,766,907 | 8/1988 | de Groot et al. | 128/754 |
| 4,790,329 | 12/1988 | Simon | 128/749 |
| 4,799,495 | 1/1989 | Hawkins et al. | 128/754 |
| 4,893,635 | 1/1990 | de Groot et al. | 128/754 |
| 4,917,100 | 4/1990 | Nottke | 128/749 |
| 4,958,625 | 9/1990 | Bates et al. | 128/754 |
| 4,976,269 | 12/1990 | Mehl | 128/754 |
| 5,031,634 | 7/1991 | Simon | 128/754 |
| 5,195,533 | 3/1993 | Chin et al. | 128/754 |
| 5,353,804 | 10/1994 | Kornberg et al. | 128/754 |
| 5,409,013 | 4/1995 | Clement | 128/753 |

*Primary Examiner*—Max Hindenberg
*Attorney, Agent, or Firm*—Cowan, Liebowitz & Latman, P.C.

[57] ABSTRACT

This invention concerns an improved multiple biopsy gun to collect tissue samples having a housing and an axially elongated cutting needle and stylet extending from the housing, wherein the housing contains a driving mechanism which propels the stylet and the cutting needle forward in sequential fashion to capture two or more tissue samples, without the necessity to reload the biopsy gun or to remove the biopsy gun from the target site between biopsies.

6 Claims, 5 Drawing Sheets

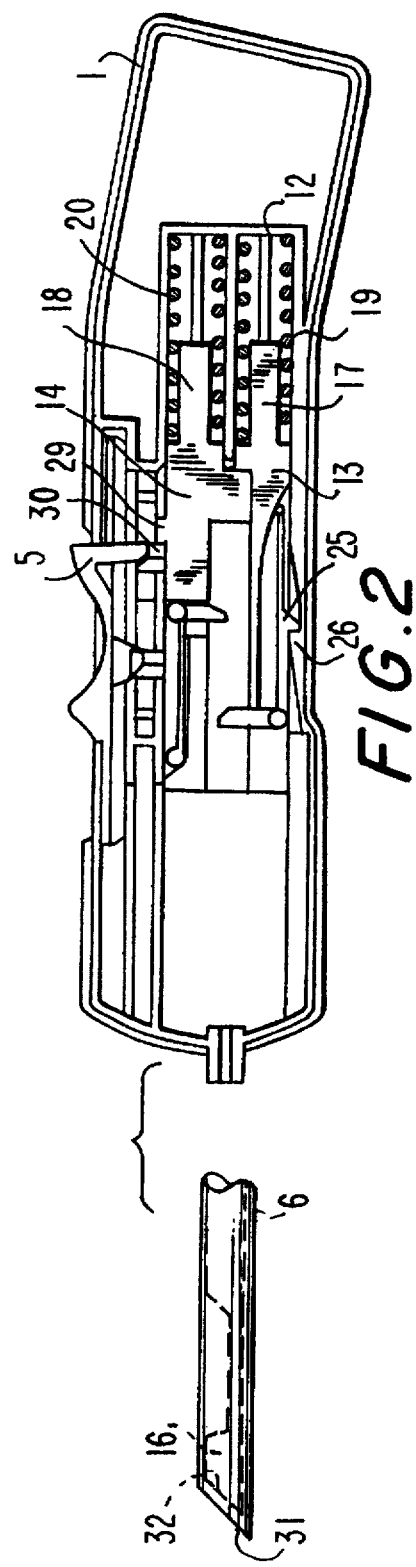
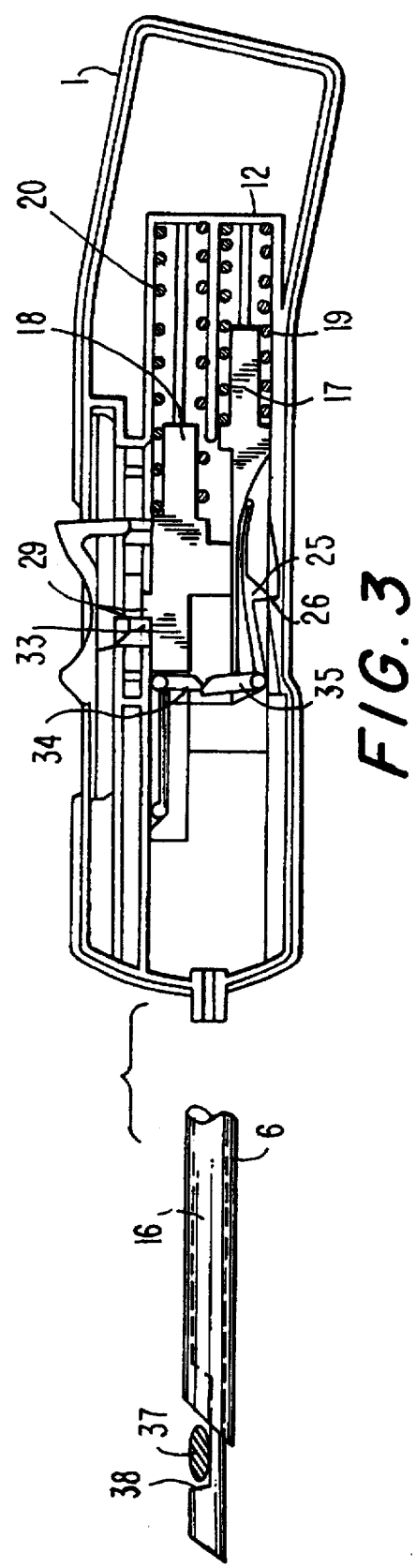

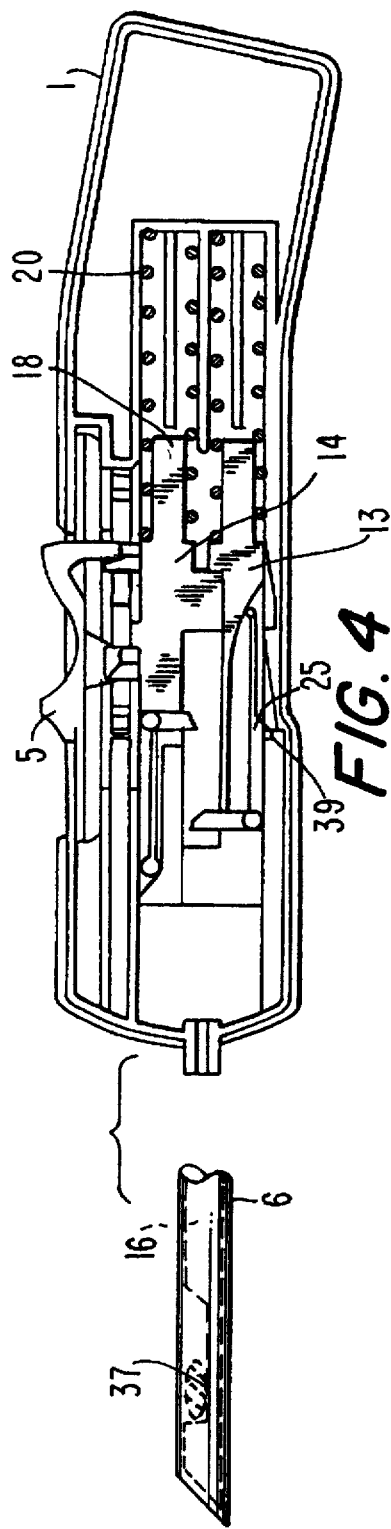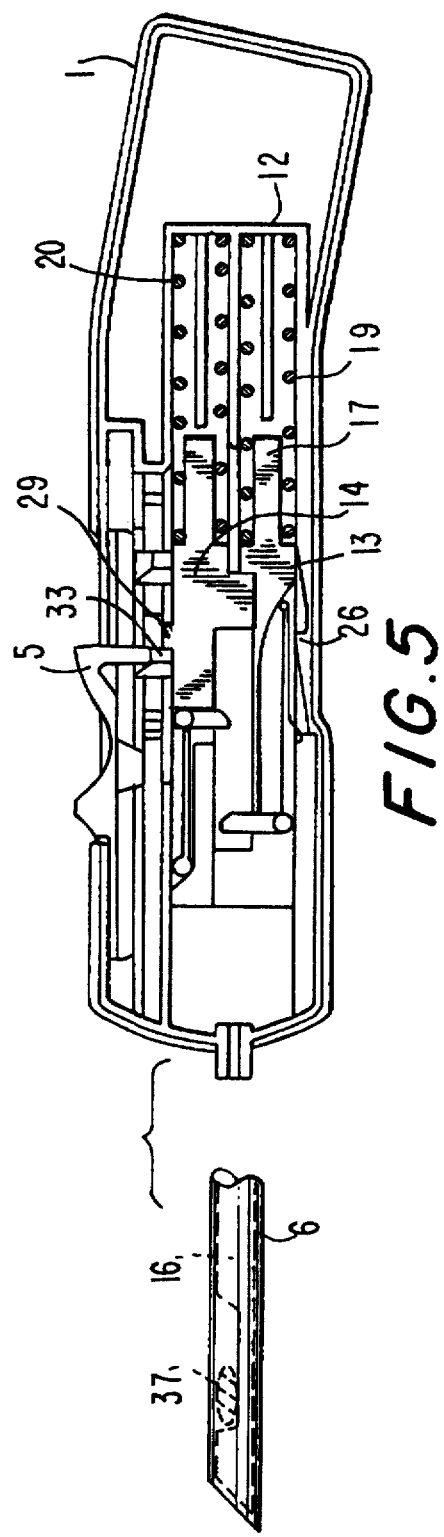

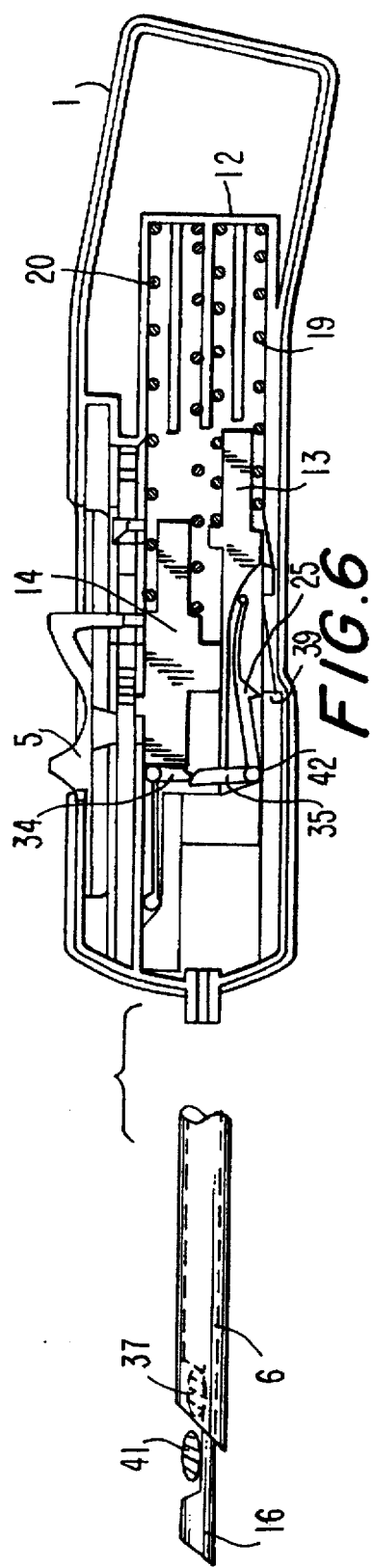
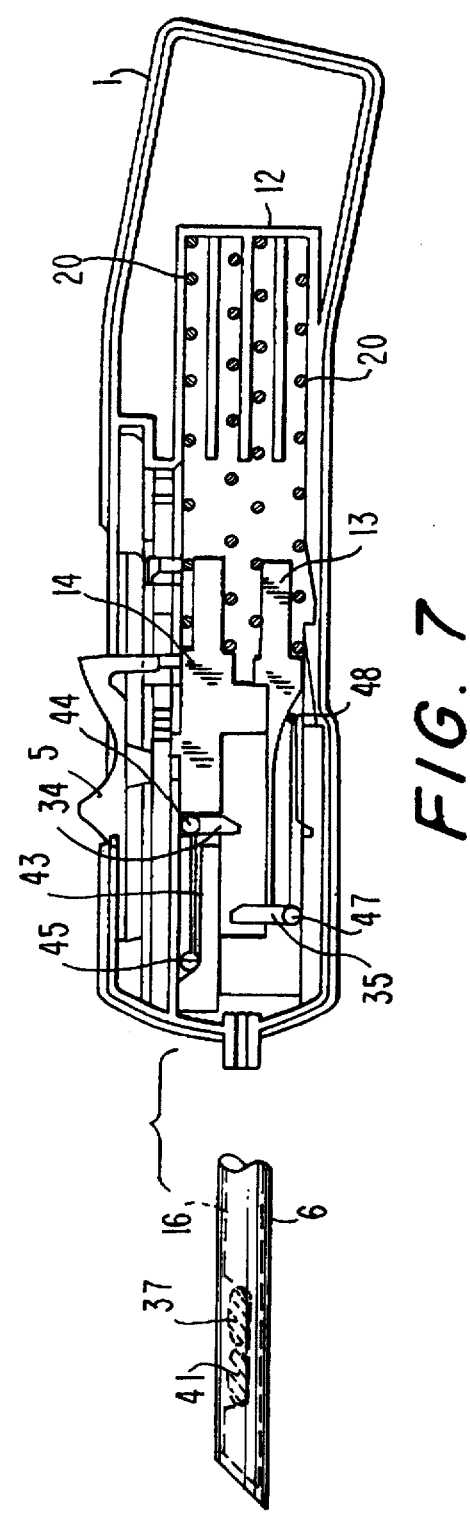

SINGLE PUNCTURE MULTI-BIOPSY GUN

FIELD OF THE INVENTION

This invention relates to an improved automatic biopsy gun, wherein the improvement enables multiple biopsy performance at one puncture without the need of gun reloading during the procedure. This invention also relates to a biopsy gun which has an anti-needle puncture safety device, which employs a simpler and safer procedure and wherein there is easy specimen removal from the gun.

BACKGROUND OF THE INVENTION

Needle biopsy procedure, used to obtain tissue specimens for microscopic examination, is well known in most fields of medicine. Non-automatic, two hands-operated biopsy needle devices include a cutting needle in which a stylet slides in and out to save the tissue cut by the biopsy needle inside the stylet notch and the cutting needle lumen. The disadvantage of this biopsy procedure is the necessity to use two hands for handling the device, making this procedure more complicated and more prone to physicians' mistakes, such as needle movement and/or incorrect biopsy.

These disadvantages promoted the development of an automatic biopsy gun in which the movements of the cutting needle and the stylet are done by pressing buttons which actuate loaded springs. The springs drive the stylet and cutting needle forward sequentially, eliminating the need for two-handed operations. An example of an automatic biopsy gun is disclosed in Bates et al., U.S. Pat. No. 4,958,625. Such an automatic biopsy gun device is now the treatment of choice for core biopsies, such as per rectum prostate biopsy to detect malignancy. However, such a biopsy gun is lacking in at least two respects:

1. There is no effective protection for doctors or patients against accidental needle puncture during a procedure (especially in prostate core biopsies without transrectal ultrasonic guidance). The doctor may be exposed to cross-contamination and infections, and the patient may be exposed to rectal wall puncture and cross-contamination.

2. Most patients require more than one needle biopsy to detect their pathology. The known manual and automatic guns are only capable of performing one biopsy per each insertion inside the body. After the biopsy is performed the steps are as follows: (A) the device is taken out of the body, (B) the device is opened by retracting the cutting needle proximally, (C) the biopsy is taken out, and (D) the biopsy gun can be loaded for a second biopsy. The length of time required for the procedure reflects the number of times the gun is introduced into the target body organ. When 10 to 12 prostate core biopsies are performed, the time of procedure is a multiple of the biopsies taken. Also, each needle puncture for getting to the target organ and obtaining a specimen increases trauma to the patient and/or site of the attempted biopsy.

A multi-biopsy gun is disclosed in U.S. Pat. No. 5,195,533, in which multiple biopsies are obtained in one body entrance puncture. According to the invention capturing multiple specimens in sequence without the need to unload each specimen is achieved by a double (or more) length of side notch stylet length and multiple gun loading and shooting once inside the target organ. According to the invention of the '533 patent, removal of the specimen is achieved by completely removing the cutting needle from the stylet notch area. The disadvantage of this device is that the gun must be loaded before each shooting. This loading, which is done while the needle is still inside the body tissue, is potentially dangerous since it requires the physician to apply force to the loaded gun which could cause accidental movement of the needle while inside the body tissue. If the gun is taken out of the body for a second loading and then reinserted into the body for a second biopsy, the advantage of single puncture multiple biopsy is negated. Thus, there would be great advantage to a single-insertion, multiple biopsy procedure without repeated spring loading inside the body.

An additional disadvantage of the multiple insertion biopsy gun of the '533 patent is the manner in which specimens are removed from the stylet notch. The biopsy gun of the '533 patent has a shooting step length of only one specimen length, and the only way to take out the second or more specimens is by moving the cutting needle forward and revealing the first or more specimen. This procedure is time consuming as well as potentially causing more damage to the first delicate tissue specimen when the long needle tube is retracted forward and creates friction with the specimen tissue.

SUMMARY OF THE INVENTION

The present invention concerns a novel biopsy gun which is capable of taking more than one biopsy with a single body puncture without the need of reloading during the procedure or the need of cutting needle retractions for specimen removal. The invention also concerns a safety mechanism to prevent accidental needle puncture during biopsy procedures.

The biopsy gun has a cutting needle through which extends a stylet needle having a side-facing notch to hold the sequentially sampled biopsied tissue.

Both the cutting needle and the stylet are each attached to springs. The biopsy procedure is effected by pressing an actuator button, thus releasing the stylet, which is propelled forward to penetrate tissue for a predetermined length correlating to the required length of biopsy. As the stylet stops moving forward, the cutting needle is propelled forward automatically to generate a tissue biopsy sample and the side notch is filled with the biopsied tissue to be removed upon retraction. A physician may choose to biopsy a second area of the same organ and can do so without the necessity of reloading the gun or springs merely by repositioning the needle and pressing the actuator button again. Upon completion of the biopsy procedure the physician withdraws the gun/needle/stylet configuration from the body. When the cutting needle is retracted, each of the biopsied tissue samples are revealed successively as they are positioned on the side notch of the stylet.

An optional protector sheath protects the physician as well as the patient from needle puncture during introduction and removal of the biopsy gun from the target organ for biopsy. The protective sheath, a rigid tube having open proximal and distal ends, is positioned circumferentially around the cutting needle. The sheath's proximal end is attached to the biopsy gun handle and its distal end extends slightly distal to the distal end of the cutting end core needle, preventing contact and puncture by the needle or the stylet.

In one embodiment of the invention the protector sheath sleeve can be retracted on demand to reveal the needle and stylet tip. In another embodiment the protective sheath cannot be retracted, but the cutting needle and stylet move a longer distance forward, compensating for the distance between the protective sheath distal opening and the tip of the needle/stylet. Insertion of the needle/stylet up to the target organ, such as per rectum prostatic biopsy, is done with the needle/stylet tip being protected by the protective sheath. Once the biopsy gun needle is in position for shooting, that is, to be propelled, the sheath can be retracted to reveal the needle/stylet tip. Alternatively, as with the other embodiment, shooting is actuated when the sleeve distal ending contacts the target organ.

BRIEF DESCRIPTION OF THE DRAWINGS

FIG. 2 represents a cross-sectional view of a biopsy gun according to the invention in a loaded, retracted mode;

FIGS. 3 to 7 show the stages of the multi-biopsy gun of FIG. 1 as it collects samples;

BRIEF DESCRIPTION OF THE INVENTION

Certain aspects of the invention can perhaps be better appreciated from the drawings, which describe the biopsy gun of the invention and the sequence steps of the multi-biopsy procedures.

Figure 1:
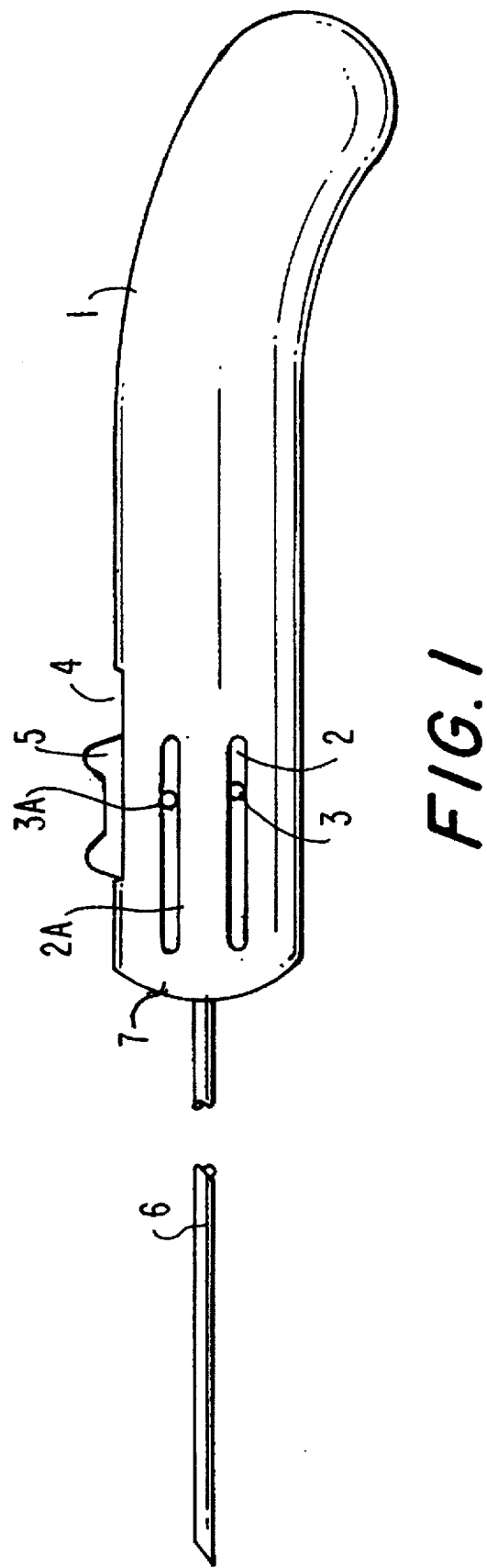
FIG. 1 is a plan view of an embodiment of the biopsy gun of the invention.

In FIG. 1 the biopsy gun housing 1, which is configured to be comfortably held by the physician, has slots 2 and 2A having levers 3 and 3A, respectively. Recess 4 contains actuator 5, which moves longitudinally within recess 4. Cutting needle 6 extends distally from the distal portion 7 of housing 1. Levers 3 and 3A are shown in an intermediate position.

The inner working of the biopsy gun can be seen in FIGS. 2 to 7. Housing 1 has an inner slide means 12, which comprises slide members 13 and 14. Slide member 13 is connected to cutting needle 6, and slide member 14 is connected to stylet 16, which moves slidingly within cutting needle 6. Reduced proximal sections 17,18 of slide members 13,14, respectively, are received within spring coils 19,20, respectively. Actuator 5 is operatively connected to slide member 14, which in turn cooperates with slide member 13, as described more fully below.

Prior to insertion of the biopsy gun needle into the body, the biopsy gun must be fully "loaded", as shown in FIG. 2. The starting position for loading is represented by the right-hand portion of FIG. 7. To prepare the biopsy gun of the invention for use, the cutting needle portion 6 of the device is loaded by pulling lever 3 in the proximal direction, as shown in FIG. 3. Lever 3 is fixedly connected to slide member 13, and as lever 3 is pulled in the proximal direction, projection 25 on slide member 13 slides over and catches the distal surface of catch or stop 26. Similarly, lever 3A, which is fixedly connected to slide member 14, is pulled in the proximal direction to load the stylet system, whereby projection 29 of slide member 14 catches on stop 30. In this condition, the distal tip 31 of cutting needle 6 extends distally a distance either equal to or slightly greater than that of the distal tip 32 of stylet 16.

To use the biopsy gun of the invention, the biopsy gun in loaded condition as shown in FIG. 2, and with actuator 5 in the forward safety position shown in FIG. 7, is manipulated to insert the cutting needle 6 into a desired site in an organ or other portion of the patient's body. The physician double checks that the distal end tip 31 of cutting needle 6 is properly positioned and then activates the biopsy gun by pulling actuator 5 proximally and then pushing actuator 5 down, that is, toward slide member 14. As actuator 5 is pushed down, stop 30 moves, thereby allowing slide member 14 to move distally until projection 29 is restrained by stop 33. Stylet 16 is propelled forward as sliding member 14 is moved by the force from coiled spring 20.

As slide member 14 moves forward, and just before the end of its distal movement as projection 29 reaches stop 33, a trigger member 34 on slide member 14 contacts release member 35. Movement of release member 35 causes projection 25 to disengage from stop 26, whereby slide member 13 is propelled forward by the force of coiled spring 19. Cutting needle 6 also is propelled forward, whereby a first tissue sample 37 is secured in the distal portion of a notch 38 in stylet 16. The forward movement of slide member 13 halts as projection 25 reaches stop 39.

In this phase the first tissue sample 37 is stored in notch 38 and could be removed if only one sample were desired.

To secure a second tissue sample the physician repositions the distal tip 31 of cutting needle 6 within the organ or body. Most significantly, there is no need to remove the biopsy gun from the patient to reload. When distal tip 31 is in position, the physician moves actuator 5 forward, that is, distally, as shown in FIG. 5, and presses down to again activate the biopsy gun. As actuator 5 is pressed down, stop 33 is released and slide member 14 is propelled distally by the force of coiled spring 20. As stylet 16 is also propelled distally, organ or body tissue causes first tissue sample 37 to move proximally within notch 38. Trigger member 34 again contacts release member 35, which in turn causes projection 25 to release from stop 39. Slide member 13 is then propelled forward by the force of coiled spring 19, together with cutting needle 6 to separate second tissue sample 41, which is then positioned adjacent first tissue sample 37 in notch 38. The forward, or distal, movement of slide member 13 and cutting needle 6 is stopped when projection 25 enters opening 42.

With regard to trigger member 34 and release member 35, it should be noted that they are portions of a clever release system for the predictably sequential movement of stylet 16 and cutting needle 6. Rigid trigger member 34 is connected to, or a continuous part of, flexible or rigid member 43, which is attached, optionally pivotably, to slide member 14 at pivot points 44 and 45. Similarly, release member 35 is connected, or a continuous part of, flexible member 46, which is pivotably attached to slide member 13 at pivot points 47 and 48. Projection 25 is located on flexible member 46. When trigger member 34 contacts release member 35 as slide member 14 moves in the distal direction, release member 35 moves counterclockwise about pivot point 47 to cause flexible member 46 to bow inward to release projection 25 from stop 26 or 39.

Figure 8A:
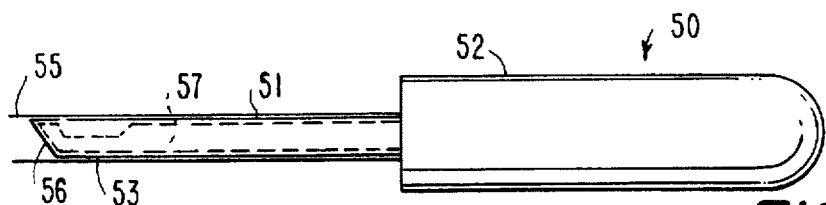
FIGS. 8A to 8C are each a schematic partial cross-sectional view of an embodiment of the invention with a fixed protective sheath.

FIG. 8A depicts a biopsy gun 50 in which a protective sheath 51 is permanently attached to housing 52. The protective sheath 51 has an inner diameter slightly larger than the external diameter of the cutting needle 53 so that the cutting needle 53 can move axially without any friction with the sheath 51. The distal tip 55 of protective sheath 51 extends slightly beyond the distal tip 56 of the cutting needle 53 and stylet 57 a distance which prevents inadvertent contact and puncture between needle 53 and/or stylet 57 and any body surface. This sheath overlap facilitates insertion until a target organ or body part is reached and handling with minimal risk of patient or physician being punctured.

Figure 8B:
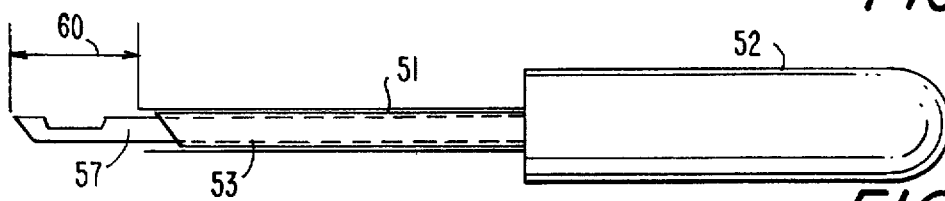

As shown in FIG. 8B, the biopsy step length 60 is long enough to enable standard length of biopsy specimen.

Figure 8C:
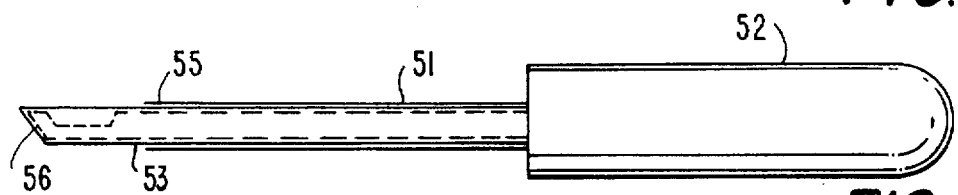

FIG. 8C depicts the relative distances between the distal tip 55 of sheath 51 and the distal tip 56 of cutting needle 53 after a first biopsy sample is taken.

Figure 9A:
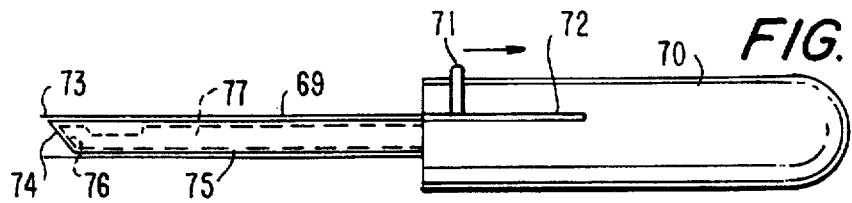
FIGS. 9A and 9B are each a schematic partial cross-sectional view of an embodiment of the invention with a retractable protective sheath.
Figure 9B:
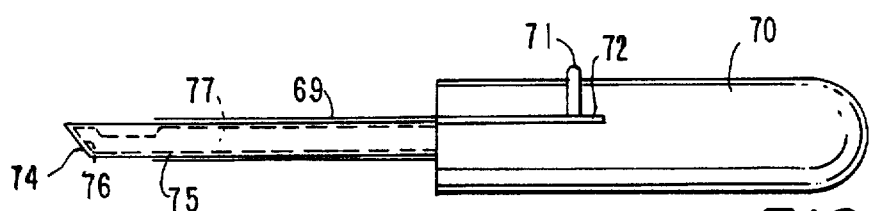

FIGS. 9A and 9B concern an embodiment of the invention where a protective sheath 69 is retractable. The biopsy gun housing 70 has a lever 71 that moves within a slot 72. Lever 71 is operatively connected to sheath 69, the distal tip 73 of which extends distally slightly past the distal tip 74 of cutting needle 75 and the distal tip 76 of stylet 77, when the biopsy gun is loaded. Proximal movement, i.e., retraction, of lever 71 within slot 72 causes sheath 69 to move proximally, thus exposing the distal tips 74,76.

It must be understood that the invention is not limited to only two sequential biopsies but more than two sequential biopsies could be performed with appropriate modification of the internal mechanism. Modification of the multi-biopsy gun described herein to collect, for example, 3 or 4 tissue samples, without reloading is well within the scope of the invention. Also, a biopsy gun that gathers only one tissue sample with the cutting needle and stylet is within the scope of this invention.

The materials to be used according to the invention would be those conventional to the field. The housing could be any rigid or substantially rigid material, such as a suitable polymer. The springs are preferably comprised of suitable metal, and the inner parts, such as slide members, are preferably of rigid metal or polymer. The cutting needle and stylet would preferably be a physiologically acceptable metal, such as stainless steel, and the optional sheath would likely be a rigid polymer. Also, while the embodiment of the invention described above employs spring coils to move the slide members, it is within the scope of the invention that the sliding members could be powered by other magnetic, mechanical, electrical, electromagnetic, or air pressure means.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A multiple biopsy gun to collect tissue samples having a housing and an axially elongated cutting needle and stylet extending from the housing, the improvement wherein the housing contains a driving mechanism which propels the stylet and the cutting needle forward in sequential fashion to capture two or more tissue samples, without the necessity to reload the biopsy gun or to remove the biopsy gun from the target site between biopsies.

2. The multiple biopsy gun of claim 1, wherein the cutting needle mechanism can be retracted to reveal the entire length of the side notch of the stylet with the multiple specimen contained therein to remove the biopsied specimen.

3. The multiple biopsy gun of claim 1, wherein the stylet can be retracted from the proximal part of the gun housing to remove the biopsied specimen located in the side notch of the stylet.

4. In a biopsy needle instrument having a housing, axially elongated stylet means extending from said housing at a proximal position for defining a specimen of a predetermined specimen length at a distal position thereof, cutting needle means coaxially extending from said housing and disposed about said stylet means for severing the defined specimen adjacent said stylet means and displacement means for moving said stylet and cutting needle means relative to each other and to said housing between extended and retracted positions, and multiple specimen capture means formed with said stylet means and cooperatively positioned with said cutting needle means for sequentially obtaining and storing multiple specimens, the improvement wherein the housing contains a driving mechanism which propels the stylet and the cutting needle forward in sequential fashion to capture two or more tissue samples, without the necessity to reload the biopsy gun or to remove the biopsy gun from the target site between biopsies.

5. In a biopsy needle instrument for capturing a plurality of sequentially biopsied, discrete specimens, each of a predetermined specimen length comprising a housing; an axially elongated stylet extending from said housing and having distal and proximal ends; a cutting needle coaxially disposed about said stylet and having distal and proximal ends; displacement means in said housing for moving said stylet and said cutting needle relative to each other and to said housing between retracted and extended positions; and a side-facing notch formed in said stylet adjacent the distal end thereof with an axial length that is greater than the predetermined specimen length, portions of said cutting needle adjacent the distal end thereof overlying said side-facing notch when said cutting needle and stylet are both in said retracted or extended positions and exposing the predetermined length of said notch at the distal end thereof when said cutting needle and said stylet are in their retracted and extended positions respectively, whereby specimens from successive biopsies are stored seriatim in said side-facing notch, the improvement wherein the housing contains a driving mechanism which propels the stylet and the cutting needle forward in sequential fashion to capture two or more tissue samples, without the necessity to reload the biopsy gun or to remove the biopsy gun from the target site between biopsies.

6. In a method for obtaining, seriatim, multiple biopsy specimens in a biopsy needle instrument including an elongated, side-facing notch formed in a stylet supported within a cutting needle wherein the stylet and cutting needle are adapted for independent displacement between retracted and extended positions and the stylet and cutting needle are in their extended and retracted positions respectively, said method comprising multiple iterations of the steps of (a) extending the cutting needle over the stylet to cover a specimen defined at the distal end of the side-facing notch; (b) retracting the stylet and cutting needle; and (c) advancing the stylet independently of the cutting needle thereby to define a successive specimen and displace previously obtained specimens axially in the notch, the improvement wherein the housing contains a driving mechanism which propels the stylet and the cutting needle forward in sequential fashion to capture two or more tissue samples, without the necessity to reload the biopsy gun or to remove the biopsy gun from the target site between biopsies.

* * * * *